United States Patent [19]
Thomas

[11] Patent Number: 5,923,419
[45] Date of Patent: Jul. 13, 1999

[54] SYSTEM AND METHOD FOR OPTICAL INSPECTION OF RECESSED SURFACES

[75] Inventor: Alan E. Thomas, Clearwater, Fla.

[73] Assignee: Insight Control Systems International, Safety Harbor, Fla.

[21] Appl. No.: 08/876,796

[22] Filed: Jun. 16, 1997

[51] Int. Cl.[6] .................................................. G01N 21/00
[52] U.S. Cl. ................................... 356/239.4; 356/239.5; 356/240.1
[58] Field of Search ............................ 356/240.1, 239.4, 356/239.5

[56] References Cited

U.S. PATENT DOCUMENTS

| | | | |
|---|---|---|---|
| 4,606,635 | 8/1986 | Miyazawa et al. | 356/240.1 |
| 4,733,973 | 3/1988 | Machak et al. . | |
| 4,758,084 | 7/1988 | Tokumi et al. | 356/240.1 |
| 4,778,999 | 10/1988 | Fisher . | |
| 4,791,287 | 12/1988 | Fisher . | |
| 4,899,573 | 2/1990 | Dimmick et al. . | |
| 5,030,823 | 7/1991 | Obdeijin | 356/240.1 |
| 5,220,400 | 6/1993 | Anderson et al. | 356/240.1 |
| 5,365,084 | 11/1994 | Cochran et al. . | |
| 5,388,707 | 2/1995 | Stivison et al. . | |
| 5,451,773 | 9/1995 | Triner et al. | 356/240.1 |
| 5,532,605 | 7/1996 | Dimmick et al. . | |
| 5,558,233 | 9/1996 | Dimmick et al. . | |
| 5,592,286 | 1/1997 | Fedor | 356/240.1 |
| 5,604,442 | 2/1997 | Dimmick et al. . | |

OTHER PUBLICATIONS

Document Entitled: Cosmicar CCTV Lenses, date not available.
Document Entitled: 2/3" Fixed, date not available.

*Primary Examiner*—Robert H. Kim
*Assistant Examiner*—Amanda Merlino
*Attorney, Agent, or Firm*—Frederick L. Tolhurst

[57] ABSTRACT

An optical inspection system wherein a camera (14) images recessed surfaces of a workpiece through a lens (16). Video signals to the image are provided to a computer (30) that compares selected parameters of the image with predetermined values. Based on that comparison, computer (30) selectively signals a controller (20) to activate a rejector assembly (24). Lens (16) is a microlens of the wide angle type to provide an open image of the recessed surface to camera (14). An illumination system (54) directs diffused light through a gap (52) between the lens (16) and the workpiece (10) to illuminate the workpiece.

18 Claims, 3 Drawing Sheets

SYSTEM AND METHOD FOR OPTICAL INSPECTION OF RECESSED SURFACES

BACKGROUND OF THE INVENTION

1. Field of the Invention

The subject invention concerns automated inspection systems and, more particularly, automated systems for optically inspecting workpieces having concave surfaces or internal cavities as herein described.

2. Description of the Prior Art

Various types of systems for the inspection of workpieces having concave surfaces or internal chambers or cavities are known in the prior art. Examples of such devices include containers, molds, closures, caps, lids and items with concave surfaces as well as other similar structures. Such workpieces with internal cavities or concave surfaces are generally referred to herein as "recessed workpieces" or "workpieces with recessed surfaces."

Some known inspection systems such as illustrated in U.S. Pat. Nos. 4,733,973 and 4,899,573 are based on pressurization or physical measurement such as shown in U.S. Pat. Nos. 5,604,442; 5,558,233 and 5,532,605; and 5,388,707. Other types of inspection systems such as described in U.S. Pat. Nos. 4,791,287; 4,778,999; and 5,365,084 have relied on various types of optical schemes to inspect discrete items such as containers as well as web-type goods such as sheets of plastic or fabric.

Some optically-based automated inspection systems have employed a camera to image the inside of the item being inspected. However, such inspection systems did not work well with items of certain types as, for example, closures in which internal threads or other design features tended to obstruct the image of the recessed or internal surface of the closure, particularly in the vicinity of the seal.

To overcome some of the difficulties of camera imaging, some prior art inspection systems have employed multiple cameras with overlapping fields of vision. However, these systems were mechanically complicated and presented difficulties with image integration.

Such camera arrangements have been adequate for some circumstances where the recessed surface was substantially larger than the lens or where the light transmissivity of the workpiece was sufficient to illuminate the regions of concern. However, these prior art systems were not successful in all applications. For example, to provide illumination, prior art systems have sometimes used backlighting techniques. When the workpiece was opaque or sufficiently non-transmissive to light, backlighting techniques were not effective in illuminating the recessed surface. Indeed, in some applications it was found that backlighting could actually obscure the defects that were being sought.

Wide aperture or "fish eye" lenses have generally not been used in applications where the size of the lens was substantially equal to or even greater than the size of the recessed surface that was being inspected. In those applications it was found that the lens tended to block the illumination of the recessed surface. Consequently, the recessed surfaces could not be illuminated sufficiently to allow the recessed surface to be adequately imaged.

Accordingly, in the prior art there existed a need for an improved optical inspection system that could inspect recessed surfaces that had openings that were relatively small in comparison to the size of lenses that were generally used. In particular, there was a need for a system that could employ a wide angle lens to inspect such relatively small recessed surfaces.

SUMMARY OF THE INVENTION

In accordance with the subject invention, a method and system for optically inspecting the recessed surface of a workpiece through a camera and lens assembly wherein an illumination system has an annular light source that is located concentrically around the camera and lens assembly. The annular light source provides diffused light through a continuous gap between the lens and the workpiece to illuminate the workpiece. This illumination system provides diffused light in response to input control signals from a controller. A computer provides the output control signals to the controller in response to video signals from the camera.

Preferably, a ring reflector reflects light from the annular light source in a radially outward direction and an annular mirror reflects light from the ring reflector in a radially inward direction through the continuous gap.

More preferably, the lens is a microlens that has an area that is less than the area of the recessed surface of the workpiece.

Most preferably, the lens is a wide aperture lens having a focal length less than 9 mm.

Other objects and advantages of the invention disclosed herein will become apparent to those skilled in the art as a description of a preferred embodiment of the invention proceeds.

BRIEF DESCRIPTION OF THE DRAWINGS

A presently preferred embodiment of the invention disclosed herein is shown and described in connection with the accompanying drawings wherein.

PREFERRED EMBODIMENT OF THE INVENTION

Figure 1:
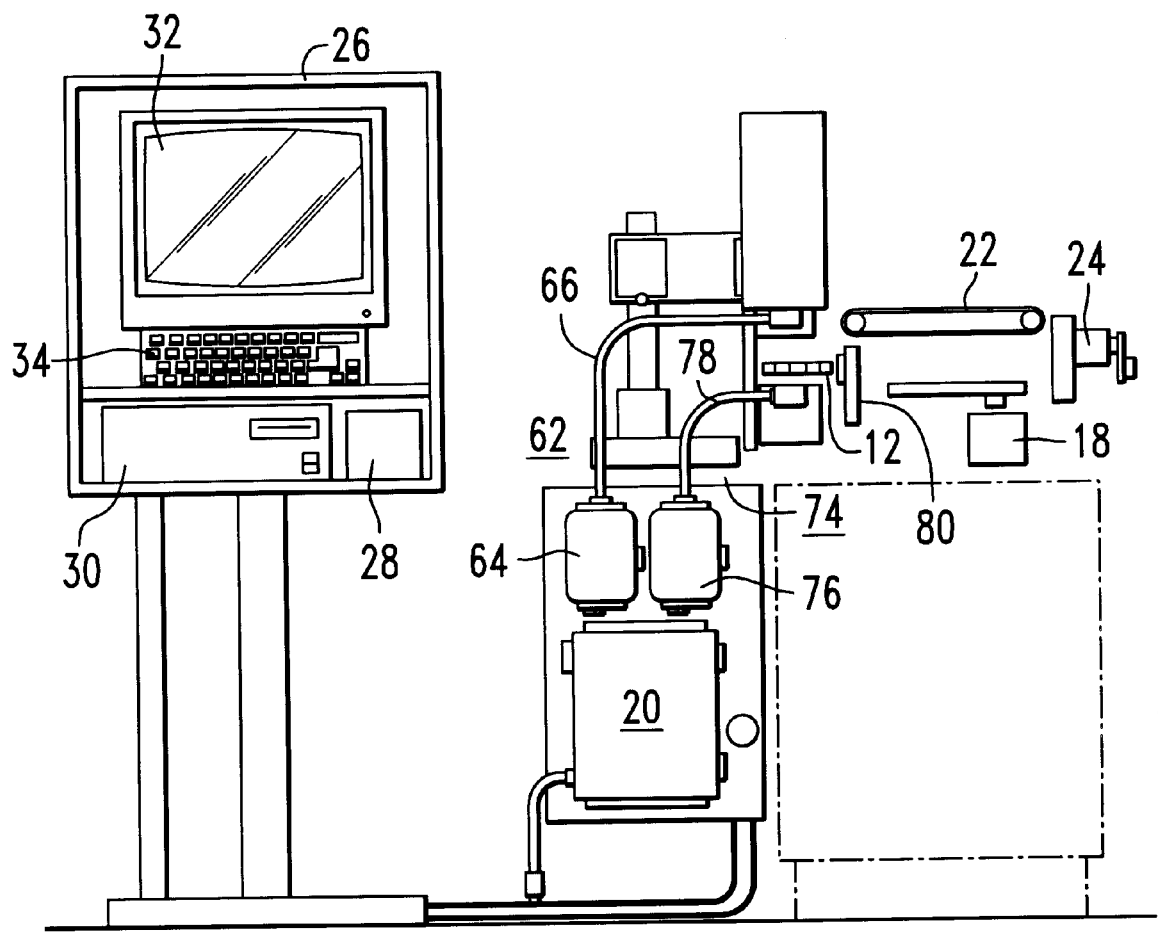
FIG. 1 is a schematic of the system and method herein disclosed for optically inspecting items with recessed surfaces.
Figure 2:
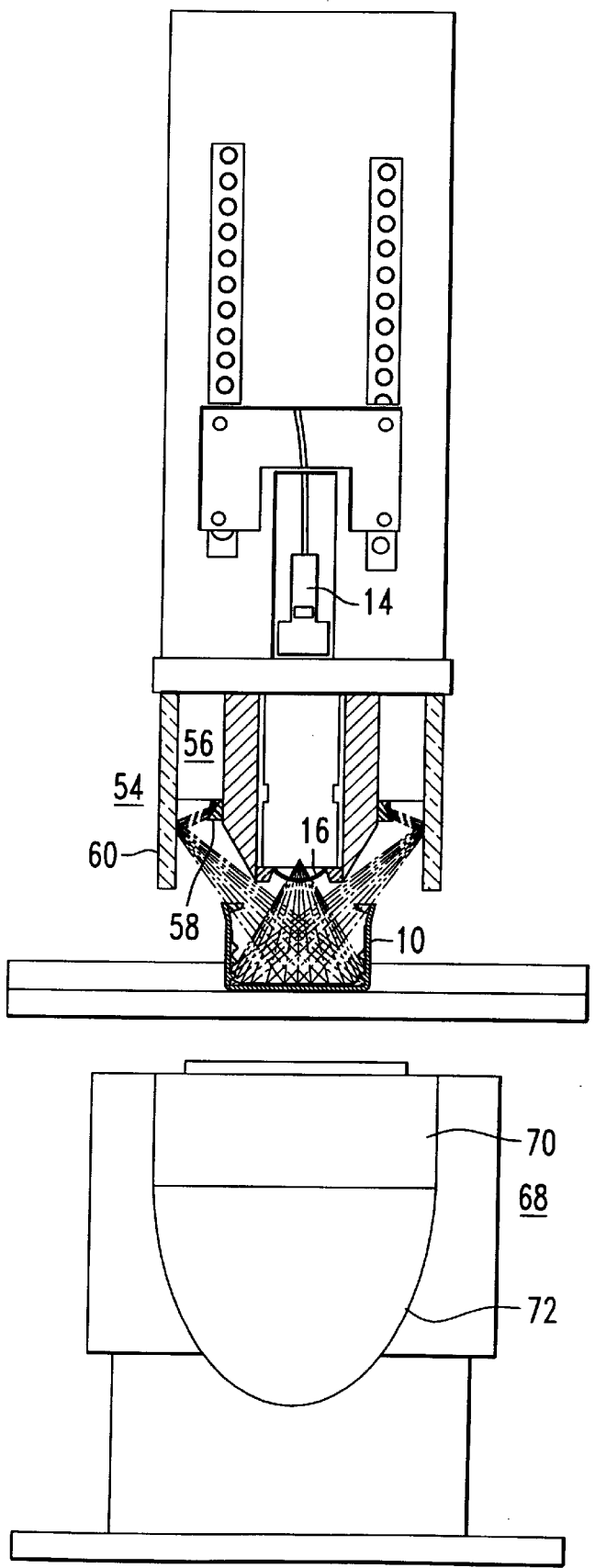
FIG. 2 is a cross-sectional view of the camera and illumination systems shown in FIG. 1.
Figure 3:
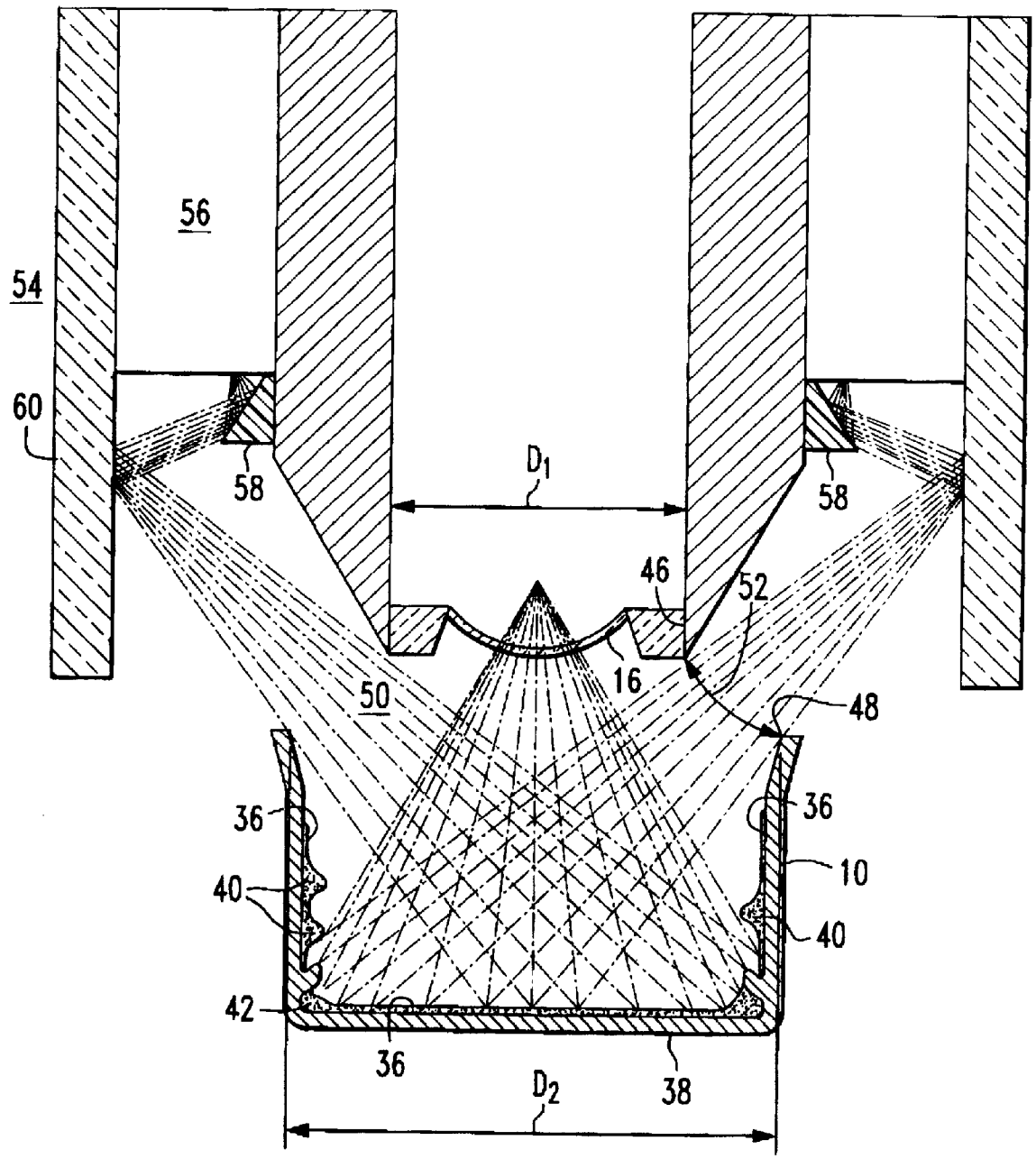
FIG. 3 is a cross-sectional view of the illumination system shown in FIG. 1 and illustrating the illumination pathways.

The preferred embodiment of the optical inspection system herein disclosed is illustrated in FIGS. 1–3. As will be understood by those skilled in the art, a workpiece such as closure 10 is delivered to a starwheel 12 in a conventional manner. Starwheel 12 advances closures 10 to an inspection location or station which is in the field of view of a camera 14 through a lens 16. An encoder 18 is electrically connected to a programmable controller 20 which monitors the location of closure 10. As well understood by those skilled in the art, encoder 18 monitors the position of starwheel 12 relative to the fixed inspection location and provides this information by an electrical input signal to programmable controller 20.

As also understood by those skilled in the art, a conveyor 22 transfers closure 10 away from starwheel 12. A rejector assembly 24 is located adjacent to conveyer 10 and is also electrically connected to controller 20. Rejector assembly 24, is an electro-mechanical device such as a solenoid or equivalent device that produces movement of a mechanical arm in response to electrical control signals from controller 20. Upon receiving a command signal from controller 20, rejector assembly 24 is activated to cause the mechanical arm to intercept a selected closure 10. In this way, command signals from controller 20 cause closures that have been found to be defective to be separated from closures that have passed acceptance tests as hereinafter more fully explained.

In accordance with the disclosed invention and as more particularly shown in FIGS. 2 and 3, at the inspection location closure 10 is positioned in the field of view of camera 14. Camera 14 images closure 10 through lens 16. Camera 14 is connected to a user interface 26. User interface 26 includes a frame grabber 28 that is connected to a computer 30 as is known to those skilled in the art. Video signals representing the image of the closure are transmitted from camera 14 to the frame grabber 28 which stores the image information. Computer 30 communicates with frame grabber 28 to compare the closure image to predetermined image parameters. Such parameters are empirically determined and are selected to identify manufacturing defects such as flash, non-fills, voids, bubbles, and black specks. Based on that comparison, computer 30 determines where the predetermined parameters of the stored image are within tolerance limits. If the closure image is not within tolerance limits, computer 30 transmits a signal to controller 20 and controller 20 activates rejector assembly 24 to cause the closure to be rejected. If the closure image is within tolerance limits, computer 30 transmits no signal and closure 10 is retained.

The predetermined parameters that computer 30 uses for comparison are subject to modification. User interface 26 further includes a monitor 32 and a keyboard 34. Both monitor 32 and keyboard 34 are electrically connected to computer 30. Monitor 32 is responsive to electrical output signals from computer 30 to produce visual images on a monitor screen. Also keystrokes by a human operator to keyboard 34 are translated to electrical signals and provided as input control signals to computer 30. In this way, the operator can affect the operation of computer 30 such as, for example, by modifying certain parameters and parameter values on which computer 30 makes an acceptance/rejection comparison.

As more specifically shown in FIGS. 2 and 3, closure 10 that is illustrated is a threaded cap having an inner surface 36 and an outer surface 38. Inner surface 36 comprises the recessed surface of this workpiece and has internal threads 40 and a seal 42. Threads 40 tend to obscure seal 42 from the field of view of camera 14 as well as cause difficulty in sufficiently illuminating seal 42 so that camera 14 can produce a clear image to the frame grabber 28.

To more fully image and illuminate the interior of closure 10, camera 14 is provided with a microlens 16 which is also a wide angle lens such as manufactured by Elmo Co., Ltd. or equivalent. As used herein, "microlens" means a small diameter, short focal length lens. Microlens 16 has a small area or diameter $D_1$ in comparison to the area or diameter $D_2$ of closure 10. Thus, the peripheral edge 46 of microlens 16 cooperates with the perimeter 48 of opening 50 in closure 10 to define an annular gap 52 between microlens 16 and closure 10. In the example of the preferred embodiment, annular gap 52 proceeds continuously around the perimeter of microlens 16. Since microlens 16 and closure 10 are of a generally circular shape, annular gap 52 has a substantially constant width as the gap proceeds around the periphery of microlens 16. However, where non-circular workpieces are inspected, the gap 52, although still continuous, would not be of a generally constant width.

FIGS. 2 and 3 further illustrate an illumination system 54 that includes an annular light source continuation with an optical means. The annular light source is responsive to an input signal to provide an output of diffused light. The optical means directs this diffused light output of the annular light source through the gap between microlens 16 and closure 10.

In the example of the presently preferred embodiment, annular light source 56 comprises a ring light of the type such as available from Fostec or equivalent. However, in other embodiments, alternative devices such as a strobe bulb designed in the shape of a ring could also be used. Annular light source or ring light 56 is located concentrically around camera 14. Ring light 56 emits an output illumination signal of diffused light in response to input signals. The optical means for directing the output illumination signal of ring light 56 includes a circular reflector 58 made of diffused plastic material and an annular mirror 60. As illustrated in FIG. 2, reflector 58 is an angled diffuser that reflects light from ring light 56 in a generally radially outward direction and mirror 60 reflects light from reflector 58 in a generally radially inward direction. The optical means directs output illumination from ring light 56 through the annular gap 52 and is incident to the inner surface 36 of closure 10 at a non-normal angle. In this way, output illumination from ring light 56 illuminates the inner surface 36 of closure 10.

Ring light 56 is responsive to input light signals from a strobe assembly 62. Strobe assembly 62 includes a light pulse generator 64 and a means for conducting light from the output of light pulse generator 64 to ring light 56 such as fiberoptic bundle 66. In the presently disclosed embodiment, light pulse generator 64 is of the type such as is available from EG&G Company or equivalent that produces a pulse of light in the visible or infrared spectrum in response to an electrical trigger signal. Light pulse generator 64 is electrically connected to controller 20 and controller 20 provides trigger signals to generator 64 in coordination with the imaging by camera 14. Thus, when controller 20 determines that a closure 10 is positioned for imaging in the field of view of camera 14, controller 20 sends a trigger pulse to generator 64 causing it to generate a light signal that is conveyed to ring light 56 through bundle 66. As previously explained, the illumination signal from ring light 56 then illuminates closure 10.

As also shown in FIG. 3 of the disclosed embodiment, a second illumination system 68 includes an annular light source 70 in combination with optical means for directing light from the annular light source 70 toward lens 16.

Illumination system 68 is located in opposing relationship to camera 14 and is oriented to direct diffused light in the direction of lens 16. Annular light source 70 is a ring light although other light sources could also be used. Annular light source or ring light 70 provides diffused light in response to light input signals. The output light from ring light 70 is reflected by a parabolic mirror 72 and redirected toward lens 16. In this way, light from a parabolic mirror 72 illuminates the outer surface 38 with closure 10 to provide backlighting illumination of the workpieces.

Second illumination system uses a ring light 68 is of a type similar to ring light 56 and emits diffused light in response to light input signals. Also similarly, ring light 70 is connected to a second strobe assembly 74 that includes a light pulse generator 76 that provides pulses of light in response to electrical input signals. Second strobe assembly 74 also includes a fiberoptic bundle 78 or equivalent means for conducting light from light pulse generator 76 to ring light 70. Light pulse generator 76 is electrically connected to controller 20. Controller 20 provides trigger signals to generator 76 and an illumination pulse is transmitted through fiberoptic bundle 78 to ring light 70. Due to the location of ring light 70, this provides backlighting of closure 10 during the imaging process.

In accordance with the pulse-type illumination of said closure 10, a sensor assembly 80 is also located at the imaging location. Sensor assembly 80 is of the type that is available from Banner Company or Sick Company or equivalent to detect the position of closure 10. Sensor assembly 80 is electrically connected to controller 20 and provides a signal to controller 20 to initiate the firing signals to light pulse generators 64 and 76.

It is preferred that lens 16 is a microlens where the lens is of sufficiently small size that it is small in comparison to the size of the recessed surface that is being inspected. More preferably, it is also preferred that the lens have a focal length in the range of 2 to 9 mm and more preferably in the range of 3 to 7 mm and most preferably a focal length of substantially 4 mm. This relatively small lens allows lens 16 to be positioned close to the workpiece without blocking the pathway for illumination of the recessed surface through the continuous gap between the lens and the workpiece. The wide angle or short focal length of lens 16 provides a flattened or opened image of the recessed surface image of the workpiece to camera 14. This type of image has been found to afford more precise comparisons by computer 30.

As will be apparent to those skilled in the art, other embodiments of the invention disclosed herein may be included within the scope of the following claims.

I claim:

1. A system for optically inspecting a workpiece having a recessed surface as the workpiece is conveyed past an inspection location, said system comprising:
   a microcamera and microlens assembly that is positioned at the inspection location to image the recessed surface of said workpiece, the diameter of said microlens being less than the diameter of the recessed area of said workpiece;
   an illumination system having an annular light source that is located concentrically around the microcamera and microlens assembly and that provides diffused light in response to input signals, wherein the perimeter of said microlens and the perimeter of the recessed surface define a continuous gap therebetween and the diffused light from said illumination system passes through said continuous gap to illuminate the recessed surface of said workpiece.
   a controller that is electrically connected to said illumination system, said controller providing input signals to said illumination system to cause said illumination system to produce diffused light at times when the workpiece is positioned at the inspection location; and
   a user interface that provides electrical signals to said controller in response to video signals from said microcamera and microlens assembly.

2. The system of claim 1 wherein the continuous gap between the perimeter of said microlens and the perimeter of the recessed surface comprises an annular gap.

3. The system of claim 1 wherein said illumination system includes optical means for directing the diffused light of said annular light source through said continuous gap.

4. The system of claim 3 wherein said optical means comprises:
   a ring reflector that receives light from the annular light source and reflects the light in a radially outward direction; and
   an annular mirror that receives light reflected from the ring reflector and reflects it in a radially inward direction through the continuous gap.

5. The system of claim 4 wherein said ring reflector is generally circular and is concentrically located around said microcamera and microlens assembly.

6. The system of claim 5 wherein said annular mirror is generally circular and is concentrically located around said microcamera and microlens assembly at a radius that is greater than the radius of said ring reflector.

7. The system of claim 1 wherein said microlens has a focal length less than 9 mm.

8. The system of claim 7 wherein said annular light source comprises a ring light and wherein said illumination system includes a light pulse generator that produces an optical illumination signal in response to an electrical trigger signal and wherein said illumination system includes means for conducting the illumination signal from the light pulse generator to said ring light.

9. A system for inspection of workpieces having a recessed surface, said system comprising:
   a microcamera and microlens assembly for imaging said recessed surfaces, said microcamera and microlens assembly having a perimeter that cooperates with the perimeter of the recessed surface to define a continuous gap therebetween;
   a ring light that is located concentrically around said microcamera and microlens assembly, said ring light emitting diffused light in response to light input signals;
   optical means for directing the output illumination of said ring light through the continuous gap to illuminate the recessed surface;
   a strobe assembly, said strobe assembly including a light pulse generator that provides a light signal output in response to electrical input signals, said strobe assembly also including means for conducting light from the light pulse generator to said ring light;
   a controller that is electrically connected to said strobe assembly, said controller providing electrical signals to said strobe assembly in correlation with the position of the workpiece to cause said light pulse generator to produce a light signal output at times when the workpiece is in the field of view of said microcamera and microlens assembly; and
   a user interface that is electrically connected to said microcamera and microlens assembly and to said controller, said user interface comparing image information received from said microcamera to predetermined image parameters and providing rejection command signals to said controller in accordance with such comparison.

10. The inspection system of claim 9 further comprising:
   a second illumination system that is disposed opposite from the microcamera and microlens assembly and oriented such that said second illumination system directs diffused light in the direction of said microcamera and microlens assembly in response to light input signals, said second illumination system including a second ring light that emits diffused light in response to light input signals, said second illumination system also including second optical means for directing the diffused light of said second ring light; and
   a second strobe assembly, said second strobe assembly including a second light pulse generator that provides a light output signal in response to an electrical input signal, said second strobe assembly also including means for conducting light from the output of the second light pulse generator to said second ring light.

11. The inspection system of claim 10 wherein said microlens has a focal length less than 9 millimeters.

12. A system for inspection of a workpiece having a recessed surface, said system comprising:

a microlens for imaging the recessed surface of the workpiece, said microlens being located adjacent to the recessed surface of said workpiece, the perimeter of said microlens cooperating with the perimeter of the recessed surface to define a continuous gap therebetween;

a first annular light source that is located concentrically around said microlens, said first annular light source including a first ring light that emits diffused light in response to light input signals, and also including a first optical means that is to light emitted from said first ring light to direct diffused light from said ring light through said continuous gap;

a first strobe assembly, said first strobe assembly including a light pulse generator that provides pulses of light in response to electrical input signals, said first strobe assembly also including means for conducting light that is generated by the light pulse generator from the light pulse generator to said first ring light;

a second annular light source that is oriented in opposed relationship to said microlens, said second annular light source including a second ring light that emits diffused light in response to light input signals and including second optical means for directing the output illumination of said ring light;

a second strobe assembly, said second strobe assembly including a second light pulse generator that provides pulses of light in response to electrical input signals, said second strobe assembly also including means for conducting light from the output of the second light pulse generator to said second ring light;

a controller that is electrically connected to said first and second strobe assemblies, said controller providing trigger signals to said first and second strobe assemblies to cause said first and second light pulse generators to produce output illumination signals; and a user interface that is electrically connected to said microcamera and to said controller, said user interface having a video processing unit that compares image information from said microcamera to predetermined image parameters, said video processing unit including a frame grabber that is connected to the microcamera and microlens assembly and that is responsive to video signals from said microcamera and microlens assembly to store image information, and a programmable computer that is connected to the frame grabber, and that is responsive to output signals from the frame grabber to compare the workpiece image with predetermined image parameters and to provide a rejection command signal to said controller in accordance with said comparison, said user interface further including a video monitor and a keyboard that are electrically connected to said programmable computer, said monitor producing visual images in response to signals from said computer and said keyboard providing signals to said computer in response to commands from an operator to modify the predetermined image parameters of said computer.

13. The system of claim 12 wherein said optical means of said first illumination system comprises:

a ring reflector that receives light from the annular light source and reflects it in a radially outward direction; and an annular mirror that reflects light that is outwardly reflected by said ring reflector in a radially inward direction through the continuous gap between the microlens and the workpiece.

14. The system of claim 12 wherein the microlens has a focal length of less than 9 mm.

15. A camera and lens assembly for the inspection of recessed surfaces of a workpiece, said assembly comprising:

a microcamera that is located in opposition to the recessed surface;

a microlens that is located between said microcamera and the recessed surface, said microlens having a focal length of less than 9 mm such that the image of said recessed surface through said microlens is opened;

an annular light source that is concentrically located around said microcamera;

a reflector that directs light from said annular light source in a radially outward direction; and an annular mirror that reflects light from said reflector in a radially inward direction to illuminate the recessed surface.

16. A method for optically inspecting a workpiece having a recessed surface, said method comprising the steps of:

positioning a microcamera and microlens at a location adjacent to the recessed surface, said microlens cooperating with the periphery of the recessed surface to define an annular gap between the microlens and said recessed surface;

illuminating the recessed surface with a pulse of diffused light that is directed through the annular gap between the microlens and the periphery of said recessed surface;

recording the image of said recessed surface that appears on the focal side of said microlens during the period that said recessed surface is illuminated;

comparing the recorded image of said recessed surface to at least one image parameter having values within a predetermined range; and rejecting said workpiece when said recorded image is outside the range of the predetermined image parameter.

17. The method of claim 16 further comprising the step of:

illuminating the exterior of said workpiece with a pulse of diffused light that is directed toward said microlens, said exterior illuminating step occurring substantially coterminously with said step of illuminating the recessed surface of the workpiece.

18. The method of claim 16 wherein the focal length of said microlens is less than 9 millimeters.

\* \* \* \* \*